United States Patent [19]

Gits et al.

[11] 4,053,583

[45] Oct. 11, 1977

[54] LIVE NEWCASTLE DISEASE VIRUS VACCINES

[75] Inventors: Jacqueline Gits, La Hulpe; Nathan Zygraich, Bruxelles, both of Belgium

[73] Assignee: SmithKline Corporation, Philadelphia, Pa.

[21] Appl. No.: 662,770

[22] Filed: Mar. 1, 1976

[51] Int. Cl.$^2$ .................... A61K 39/32; A61K 41/00
[52] U.S. Cl. ........................................ 424/90; 424/89
[58] Field of Search ................................ 424/89, 90; 195/1.1–1.8

[56] References Cited

PUBLICATIONS

Clavell et al., Chem. Abstr. 75 No. 137866e(1971) of J. Virol. 8(4): 500–8(1971) "Relation Between the Ribonucleic Acid-Synthesizing Capacity of Ultraviolet-Irradiated Newcastle Disease Virus and Its Ability to Induce Interferon."
Huppert et al., Chem. Abstr. 76 No. 84168R(1972) of Biol. Large RNA Viruses, Symp. 1969: pp. 482–492, Pub. 1970 "Newcastle Disease Virus RNA Synthesis in Cells Infected with Unirradiated or UV-Irradiated Virus."
Meager et al., Nature 235: pp. 280–282 Feb. 4, 1972 "Production of Interferon by Ultraviolet Radiation Inactivated Newcastle Disease Virus."
Preble et al., Chem. Abstr. 76 No. 96836v(1972) of J. Virol 9(2): pp. 200–206 (1972) and Chem. Abstr. 79 No. 89428x(1973) of J. Virol. 12(3): pp. 472–480 (1973) "Temperature-Sensitive Mutants Isolated From L Cells Persistently Infected with Newcastle Disease Virus."

*Primary Examiner*—Shep K. Rose
*Attorney, Agent, or Firm*—Janice E. Williams; William H. Edgerton; Alan D. Lourie

[57] ABSTRACT

The improved live Newcastle disease virus vaccines of the invention contain a cold or cold and temperature-sensitive strain of Newcastle disease virus obtained by U.V. or nitrous acid mutation. The vaccines are administered to chickens in the form of an aerosol.

5 Claims, No Drawings

LIVE NEWCASTLE DISEASE VIRUS VACCINES

This invention relates to a process for preparing improved Newcastle disease virus (NDV) strains for vaccinal use and to the live vaccines containing them.

Live NDV vaccines containing either lentogenic or mesogenic strains and administrable by various routes are known. Examples of known vaccinal NDV strains are the La Sota strain and the Hitchner B1 strain. For administration, the NDV vaccines are for example either suspended in the drinking water or administered as ocular or nasal drop or an aerosol.

The preferred method of vaccination for mass immunization against NDV is the application of live lentogenic viruses such as La Sota or Hitchner B1 strains in the form of an aerosol but the aerosol administration of these strains has been shown to be associated with rather important morbidity for young chickens, more particularly for very yound chickens (R. E. Gough and W. H. Allan, Vet. Rec. 95 (12), 263–65, 1974).

We have found that by mutagenic treatment of the La Sota (LS) virus strain either by exposing said strain to ultravioltet irradiation or to contact with nitrous acid, it is possible to obtain either cold strains or simultaneously cold and temperature sensitive strains which are attenuated and which upon their administration in the form of an aerosol to 1 to 8-day-old chickens do present a considerably reduced morbidity. The so-obtained strains and the vaccines containing them are thus from this viewpoint improved strains and vaccines.

By the term "cold strain", it is understood a strain which grows at significantly higher titers than the parent strains at temperatures lower than the normal growth temperature of the parent strain and by the term "temperature-sensitive strain", it is herein understood a modified virus strain, the growing capacity of which is significantly inhibited at high temperatures (more particularly at a temperature which is close to the internal temperature of the host) whereas the replication of the wild strain is not affected at the same temperatures. As a consequence of this caracteristic, the temperature-sensitive (ts) strain is able to multiply at a cold side of the body while its replication is inhibited in the warm deep organs of the host.

Cold strains of various viruses (e.g. influenza virus, poliovirus, measles virus) are known (Nature 213, 612-14, 1957, Perspective in Virology II: 90/1961, Ann. Paediat. 202(4): 241-52, 1964, and in Acta. Microbiol. Pol. 17: 313-18, 1968 there is described a NDV strain obtained from the mesogenic Roakin strain by 30 passages in chicken embryos at 29°-30° C but the so-called strain does not present modified growth characteristics at this temperature so that is is not a cold strain.

The present invention thus relates to a process for preparing immunogenic Newcastle disease virus strains which present a considerably reduced morbidity in 1 to 8-day-old chickens upon aerosol administration, said process consisting of inducing from a still pathogenic ND virus strain —more preferably from a vaccinal but still pathogenic ND virus strain, e.g. the La Sota ND virus strain— by mutagenic treatment —e.g. by ultraviolet irradiation or by treatment with buffered nitrous acid solution— in operative conditions which reduce the initial virus titer by 3 to 4 $\log_{10}$ and isolating from the surviving virus population a cold mutant showing at 26° C a growth which is significantly higher than the growth of the parent strain at this temperature, said cold mutant being preferably also a temperature-sensitive mutant, the growth of which is significantly inhibited at 41° C (+ 1° C).

In the process of the invention, the mutagenic treatment is for instance performed either by exposing to any laboratory ultraviolet lamp an initial virus population of $10^{9.5}$ for a duration and at a distance such that the surviving virus population be about $10^{6.5}$ or by maintaining the starting strain in contact for 2 to 5 minutes with a buffered nitrous acid solution, preferably a 4 molar solution, at a pH comprised between 4 and 4.4, e.g. for 3 minutes with a 4 molar sodium nitrite aqueous solution in molar acetic acid/sodium acetate buffer, the pH of the medium being 4.2.

The virus mutants are isolated according to any process obvious to those skilled in the art e.g. by performing several passages in embryonated chicken eggs at 26° C followed by cloning at 26° C by diluting the allantoic fluid material to such degree that one egg out of ten gives a positive response.

An example of starting material is the La Sota strain which has been deposed at the WHO collaborating Centre for Collection and Evaluation of Data on Comparative Virology at the Institut fur Medizinische Mikrobiologie, Infektionsund Seuchenmedizin der Ludwig-Maximilians Universitat (Munchen, W. Germany) where it received accession number P/76/3. Two cold strains of Newcastle disease virus obtained according to the process of this invention have been deposited at the same WHO collaborating Centre for Collection and Evaluation of Data on Comparative Virology where they received accession numbers P/76/4 and P/76/5 respectively.

For large scale production of a vaccine according to the invention, the cold or cold and temperature-sensitive mutant is grown in specific-pathogen-free (SPF) embryonated chicken eggs at a temperature between 34° and 37° C from which the virus is harvested e.g. after a three-day incubation period. The harvested virus is then preferably supplemented with a stabilizing solution —examples of stabilizing solution are peptone or arginine or sucrose, or preferably mixtures thereof, in water— distributed in glass vials and freeze-dried. The vaccine is kept in freeze-dried form in the tightly stoppered vials and rehydrated before administration.

The vaccines of this invention are thus improved vaccines against Newcastle disease and administrable in the form of an aerosol comprising a pharmaceutical diluent for aerosol administration and an effective dose of an attenuated cold strain —e.g. the NDV P/76/4 strain—, more particularly a cold and temperature-sensitive strain —e.g. the NDV P/76/5 strain— obtained from a Newcastle disease virus strain —more particularly the NDV P/76/3 strain— by ultraviolet or nitrous acid mutagenesis thereof. The improved NDV vaccines of the invention are prepared by a process which comprises inducing from a still pathogenic ND virus strain —more particularly from a vaccinal but still pathogenic ND virus strain, e.g. the P/76/3 NDV strain— by mutagenic treatment —e.g. by ultraviolet irradiation or by treatment with buffered nitrous acid solution— in operative conditions which reduce the initial virus population by 3 to 4 $\log_{10}$, isolating from the surviving virus population a cold mutant showing at 26° C a growth which is significantly higher than the growth of the parent strain at this temperature and preparing therewith according to any technique known to the art a live vaccine administrable in the form of an aerosol, said vaccine being preferably freeze-dried and more particularly freeze-dried after addition of a stabilizer.

The improved vaccines of this invention can be mixed with any other live vaccine or vaccines against avian respiratory diseases —e.g. avian infectious bronchitis vaccine— administrable in the form of an aerosol.

For vaccination, the vaccine is rehydrated and administered to the chicken according to the well known method of NDV vaccine administration in the form of an aerosol.

According to this embodiment, the invention relates to the method for immunizing chickens against Newcastle disease virus, said method consisting of administering to said chickens in the form of an aerosol an effective dose of an improved vaccine as hereinabove described.

The following examples illustrate the present invention and should not be construed as limiting its scope.

EXAMPLE 1

One milliliter of chicken egg's allantoic fluid containing 9.5 $\log_{10}$ of P/76/3 strain viruses/ml. is exposed for 10 minutes to U.V. irradiation at a distance of 15 cm from a Mineralight A 52 U.V. lamp, resulting in a virus loss of 3 $\log_{10}$.

The U.V. treated suspension is inoculated into the allantoic fluid of 9–11 day-old embryonated eggs and incubated at 26° C for 6 days. The harvested undiluted allantoic fluid material is submitted first to three further passages in the same conditions and thereafter to three other passages at 26° C, using allantoic fluid material diluted from $10^{-3}$ to $10^{-6}$ respectively.

The virus harvested from the seventh passage is cloned at 26° C by diluting the allantoic fluid material to such degree that one egg out of ten gives a positive response.

Two strains obtained according to the hereinabove treatment are labelled RIT 4029 and P/76/5 respectively and further characterized.

EXAMPLE 2

One milliliter of chicken egg's allantoic fluid containing 9.5 $\log_{10}$ of P/76/3 strain viruses/ml. is mixed with 0.5 ml. of a 4 M sodium nitrite aqueous solution in 0.5 ml. of molar acetic acid/sodium acetate buffer, the final pH being 4.2. The mixture is allowed to react for 3 minutes at room temperature (about 20° C) and the reaction is then stopped by dropwise addition of normal sodium hydroxide with stirring up to reaching pH 7.5. Such treatment results in a virus loss of 4 $\log_{10}$. The resulting virus suspension is submitted to a total of seven passages and cloned as in example 1. From the obtained clones, one is selected, labelled P/76/4 and further characterized.

EXAMPLE 3

Characteristics of the RIT 4029, P/76/4 and P/76/5 strains a. cold characteristics Virus production of the P/76/3, RIT 4029, P/76/4 and P/76/5 strains has been determined in embryonated chicken eggs at cold (26° C) and normal temperature. The results are summarized in following Table I.

TABLE I

| Strain | Infectious titre in eggs (x) | |
|---|---|---|
| | after 6 days at 26° C | after 4 days at 37° C |
| P/76/3 | 2.3 | 8.7 |
| RIT 4029 | 4.0 | 8.2 |
| P/76/4 | 6.5 | 8.3 |
| P/76/5 | 4.0 | 8.0 |

(x) expressed as $\log_{10}$EID(egg infective dosis)$_{50}$/0.2 CC.

As shown in the above Table I, RIT 4029, P/76/4 and P/76/5 strains are cold strains.

b. "ts" character of the P/76/5 strain

To test the temperature-sensitive (ts) character of the mutated strain, this strain is propagated in chicken embryo fibroblasts (CEF) at 35° and 41° C and the virus produced after 3 days at these temperatures is titrated at 35° C in CEF. The results are summarized in following Table II.

TABLE II

| Strain | Virus yield at : | | |
|---|---|---|---|
| | 35° C | 41° C | Δ35° C/41° C |
| P/76/3 | 3.2 | 3.2 | 0 |
| P/76/5 | 2.29 | 0.5 | 1.79 |

It appears from Table II that the P/76/5 strain is thermosensitive and is significantly inhibited at 41° C.

EXAMPLE 4

Each of the ND virus RIT 4029 and P/76/5 strains obtained in example 1 and P/76/4 strain obtained in example 2 is cultivated in SPF embryonated chicken eggs at 34°–37° C for 3 days and the harvested supernatant is supplemented with a stabilizing solution consisting of peptone (10% W/V), arginine (3% W/V) and sucrose (5% W/V). The mixture is distributed in 5 ml. glass vials containing $10^9$ EID$_{50}$ per milliliter each and freeze-dried and the vials are tightly stoppered to constitute multiple doses of vaccine for administration in aerosol form.

EXAMPLE 5

Clinical trials of the NDV RIT 4029, P/76/4 and P/76/5 strains

For testing the innocuity of the NDV RIT 4029, P/76/4 and P/76/5 strains, samples of vaccines prepared therefrom according to example 4 have been administered to different groups of 40 SPF one-day-old and 40 SPF 8-day-old chickens by aerosol technique, using therefore a TURBAIR aerosol generator manufactured and sold by TURBAIR Ltd, Britannica Works, Waltham Abbey, Essex, England, the final concentration being $10^{7.5}$ EID$_{50}$ per cubic foot of air in the vaccination room.

A group of 40 SPF one-day-old chickens and a group of 40 SPF 8-day-old chickens were vaccinated in the same conditions with the P/76/3 strain, as control. The results are summarized in following Table III.

TABLE III

| Vaccinal strain | Age at vaccination | | | |
|---|---|---|---|---|
| | One-day-old | | 8-day-old | |
| | pathogenicity index (x) | affected animals (%) | pathogenicity index | affected animals (%) |
| P/76/3 | 0.39 | 75.7 | 0.11 | 27.5 |
| RIT 4029 | 0.27 | 57.5 | 0.00 | 0.0 |
| P/76/4 | 0.11 | 13.3 | 0.00 | 0.0 |
| P/76/5 | 0.08 | 17.5 | 0.00 | 0.0 |

(x) : pathogenicity index (PI) : calculated for a 10 days observation post-inoculation period

TABLE III-continued

| Vaccinal strain | Age at vaccination | | | |
|---|---|---|---|---|
| | One-day-old | | 8-day-old | |
| | pathogenicity index (x) | affected animals (%) | pathogenicity index | affected animals (%) |

PI : $\dfrac{\text{sum of scores}}{\text{number of observations}}$ with the score system :

morbidity = 1
mortality = 2

As indicated in above Table III, RIT 4029, P/76/4 and P/76/5 strains are markedly less pathogenic to young chickens by spray route than the parental P/76/3 strain.

For testing the immune response of young chickens stimulated by the strains of the invention, different groups of 40 SPF one-day-old and 40 SPF 8-day-old chickens were spray vaccinated using the TURBAIR aerosol generator ($10^{7.5}$ EID$_{50}$ per cubic foot of air), one group receiving the P/76/3 strain vaccine as control. The animals were bled 14 or 21 days post-inoculation (p.i.). The results which are summarized in Table IV indicate that the NDV P/76/4 and P/76/5 strains are only slightly less immunogenic than the parent NDV P/76/3 strain.

TABLE IV

| Vaccinal strain | Immunogenicity in SPF chickens | | | |
|---|---|---|---|---|
| | Age at vaccination | | | |
| | One-day-old date of bleeding | | 8-day-old date of bleeding | |
| | 14 days p.i. | 21 days p.i. | 14 days p.i. | 21 days p.i. |
| P/76/3 | 6.7 (x) | 6.7 | 8 | 7.2 |
| P/76/4 | NT | NT | 6.0 | 6.1 |
| P/76/5 | 6.8 | 6.8 | 7.4 | 6.4 |

(x) : geometric mean of hemagglutination inhibition (HI) titre expressed as log$_2$.
NT : not tested.

For testing the immunogenicity of a cold and ts strain of the invention in the presence of maternal antibodies, a group of 20 8-day-old chickens from a conventional flock were spray vaccinated using the TURBAIR aerosol generator with the P/76/5 strain ($10^{7.5}$ EID$_{50}$ per cubic foot of air) and tested for serological results. Other groups of 8-day-old chickens were treated in the same conditions with the P/76/3 strain and the Ulster 2c strain (a strain described e.g. in Vet. Rec. 95 (12): 263–65, 1974) and one group served as control. The results are summarized in the following Table V.

TABLE V

| Vaccinal strain | Immunogenicity in passively protected chickens. | | | |
|---|---|---|---|---|
| | Age at bleeding | | | |
| | One-day-old | 8-day-old | 22-day-old (=14 d. p.i.) | 27-day-old (=19 d. p.i.) |
| Control (not vaccinated | 6.7 (x) | 4.8 | 2.5 | <2 |
| P/76/3 | 6.7(x) | 4.8 | 6.1 | 6.4 |
| P/76/5 | 6.7(x) | 4.8 | 5.8 | 5.4 |
| Ulster 2c | 6.7(x) | 4.8 | 1.5 | 1.6 |

(x) : geometric mean of HI titre expressed as log$_2$.

As it appears from Table V, the P/76/5 cold and ts strain of the invention presents only slightly reduced immunogenicity compared to the parental P/76/3 strain, while the attenuated Ulster 2c strain is not immunogenic in passively protected chickens.

For testing the degree of protection afforded by the cold and ts strain of the invention, in the presence of various levels of residual maternal antibodies, groups of 60 8-day-old, and 60 21-day-old conventional chickens were spray vaccinated using the TURBAIR aerosol generator using $10^{7.5}$ EID$_{50}$ of the P/75/5 strain per cubic foot of air and were challenged 21 days later by the intranasal route with different doses of the virulent Herts 33/56 strain.

Other groups of 60 animals were vaccinated in the same way with the P/76/3 and Ulster 2c strains respectively, and also challenged by the nasal route 21 days after vaccination with the same doses of the Herts 33/56 strain; 2 groups of 25 animals were used as control.

The results are summarized in the following Table VI, from which it appears that the P/76/5 strain has a protection capacity similar to the one of the parental P/76/3 strain.

TABLE VI

| Vaccinal strain | Lethal dose of the Herts 33/56 strain in chicken vaccinated by spray with P/76/5 strain. | |
|---|---|---|
| | Age at vaccination (HI titre prior to log$_2$ vaccination | |
| | 8-day-old (4.8) | 21-day-old (1.7) |
| Control (not vaccinated) | ≦5.5 (x) | ≦6.5 |
| P/76/3 | ≧8.5 | ≧9.5 |
| P/76/5 | ≧8.5 | ≧9.5 |
| Ulster 2c | 7.15 | ≧9.5 |

(x) : expressed as log$_{10}$ EID$_{50}$.

We claim:

1. An improved vaccine against Newcastle disease comprising a pharmaceutical diluent for aerosol adminisitration and an effective dose of an attenuated cold and temperature-sensitive strain obtained from a Newcastle disease virus strain by ultraviolet mutagenesis thereof, said strain showing a significantly higher growth at 26° C than its parent strain and having a significantly inhibited growth at 41° C.

2. An improved vaccine according to claim 1, in which the attenuated cold strain is obtained from the Newcastle disease virus P/76/3 strain.

3. An improved vaccine according to claim 1, in which the attenuated cold strain is the Newcastle disease virus P/76/5 strain.

4. An improved vaccine according to claim 1, in which the vaccine is freeze-dried.

5. A method of immunizing chickens against Newcastle disease consisting of administering to said chickens in the form of an aerosol an effective dose of a vaccine according to claim 1.

* * * * *

UNITED STATES PATENT AND TRADEMARK OFFICE
CERTIFICATE OF CORRECTION

PATENT NO. : 4,053,583
DATED : October 11, 1977
INVENTOR(S) : Jacqueline Gits and Nathan Zygraich It is certified that error appears in the above-identified patent and that said Letters Patent are hereby corrected as shown below:

[73] Assignee: SmithKline Corporation
Philadelphia, Pa.

SHOULD READ

[73] Assignee: Recherche et Industrie Therapeutiques, R.I.T.,
Genval, Belgium

Signed and Sealed this

Eleventh Day of April 1978

[SEAL]

Attest:

RUTH C. MASON
Attesting Officer

LUTRELLE F. PARKER
Acting Commissioner of Patents and Trademarks